United States Patent (10) Patent No.: US 11,376,413 B2
Gartner et al. (45) Date of Patent: Jul. 5, 2022

(54) ADULT AND PEDIATRIC EXTRACORPOREAL LIFE SUPPORT SYSTEM WITH HEPARIN TREATED OXYGENATOR SURFACE AND MAGNETIC LEVITATION MOTOR

(71) Applicants: Ension, Inc., Pittsburgh, PA (US); Massachusetts Institute of Technology, Cambridge, MA (US)

(72) Inventors: Mark Gartner, Wexford, PA (US); Minkyun Noh, Cambridge, MA (US); David L. Trumper, Plaistow, NH (US)

(73) Assignees: ENSION INC., Pittsburgh, PA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 375 days.

(21) Appl. No.: 16/220,566

(22) Filed: Dec. 14, 2018

(65) Prior Publication Data
US 2019/0125946 A1 May 2, 2019

Related U.S. Application Data

(63) Continuation of application No. PCT/US2017/038019, filed on Jun. 16, 2017.
(Continued)

(51) Int. Cl.
*A61M 60/113* (2021.01)
*A61M 60/82* (2021.01)
(Continued)

(52) U.S. Cl.
CPC ........ *A61M 60/113* (2021.01); *A61M 1/3673* (2014.02); *A61M 60/205* (2021.01); *A61M 60/82* (2021.01); *A61M 1/1698* (2013.01)

(58) Field of Classification Search
None
See application file for complete search history.

(56) References Cited

U.S. PATENT DOCUMENTS 4,639,353 A 1/1987 Takemura et al.
4,975,247 A 12/1990 Badolato et al.
(Continued)

FOREIGN PATENT DOCUMENTS

JP 04235724 8/1992
WO 2017024119 2/2017
WO 2017218987 12/2017

OTHER PUBLICATIONS

Barletta N., Schob R., Design of a Bearingless Blood Pump, Proc. of the 3rd Int Symp. On Magnetic Suspension Technology, Tallahassee, 1995.

*Primary Examiner* — Jonathan M Peo
(74) *Attorney, Agent, or Firm* — Blynn L. Shideler; Krisanne Shideler; BLK Law Group

(57) ABSTRACT

A highly portable advanced adult and pediatric compact ECLS system is based around an integrated pump-oxygenator. The system includes a central a blood inlet and flow path extending along a general longitudinal axis of the system; a pump housing defining a pump inlet in fluid communication with the central blood flow path; an impeller rotationally received within the area of the pump inlet, wherein the impeller is magnetically supported and magnetically driven; an array of hollow fiber membranes configured for gas transfer within the system for oxygenation of blood flowing across the hollow fiber membranes, wherein the membranes include a covalently-bonded heparin-based bioactive surface, and wherein the blood flow path extends from the impeller to a position to flow perpendicular over the
(Continued)

array of hollow fiber membranes; and a blood outlet configured to receive blood flowing past the array of hollow fiber membranes.

20 Claims, 1 Drawing Sheet

Related U.S. Application Data

(60) Provisional application No. 62/350,810, filed on Jun. 16, 2016.

(51) Int. Cl.
*A61M 60/205* (2021.01)
*A61M 1/36* (2006.01)
*A61M 1/16* (2006.01)

(56) References Cited

U.S. PATENT DOCUMENTS

| | | | |
|---|---|---|---|
| 5,205,721 A * | 4/1993 | Isaacson | F04D 3/00 310/184 |
| 5,217,689 A | 6/1993 | Raible | |
| 5,263,924 A | 11/1993 | Mathewson | |
| 5,266,265 A | 11/1993 | Raible | |
| 5,270,005 A | 12/1993 | Raible | |
| 5,429,486 A | 7/1995 | Schock et al. | |
| 5,770,149 A | 6/1998 | Raible | |
| 5,830,370 A | 11/1998 | Maloney, Jr. et al. | |
| 6,503,450 B1 | 1/2003 | Afzal et al. | |
| 6,723,284 B1 | 4/2004 | Reeder et al. | |
| 6,730,267 B2 | 5/2004 | Stringer et al. | |
| 6,929,777 B1 | 8/2005 | Litwak et al. | |
| 6,963,222 B1 | 11/2005 | Davies, Jr. | |
| 7,927,544 B2 | 4/2011 | Federspiel et al. | |
| 9,211,369 B2 | 12/2015 | Gartner et al. | |
| 2002/0057989 A1 | 5/2002 | Afzal et al. | |
| 2004/0219059 A1 | 11/2004 | Barringer et al. | |
| 2007/0249888 A1 | 10/2007 | Wu et al. | |
| 2008/0190870 A1 | 8/2008 | Schoeb | |
| 2008/0199357 A1 * | 8/2008 | Gellman | A61M 1/1698 422/48 |
| 2009/0175762 A1 | 7/2009 | Ogihara et al. | |
| 2010/0101657 A1 | 4/2010 | Morley et al. | |
| 2010/0288703 A1 | 11/2010 | Fortenberry | |
| 2013/0343954 A1 * | 12/2013 | Gartner | A61M 1/1698 422/48 |
| 2015/0352265 A1 * | 12/2015 | Garimella | A61L 33/0029 424/423 |

* cited by examiner

ADULT AND PEDIATRIC EXTRACORPOREAL LIFE SUPPORT SYSTEM WITH HEPARIN TREATED OXYGENATOR SURFACE AND MAGNETIC LEVITATION MOTOR

RELATED APPLICATIONS

This application is a continuation of International Patent Application Serial Number PCT/US2017/038019 which published Dec. 21, 2017 as WO 2017/218987, which publication is incorporated herein by reference. International Patent Application Serial Number PCT/US2017/038019 claims the benefit of U.S. Provisional Patent Application Ser. No. 62/350,810, filed Jun. 16, 2016, entitled "Adult and Pediatric Extracorporeal Life Support System with Heparin Treated Oxygenator Surface and Magnetic Levitation Motor" which is incorporated herein by reference.

BACKGROUND INFORMATION

1. Field of the Invention

The present invention pertains to adult and pediatric extracorporeal life support systems, and more particularly to extracorporeal membrane oxygenators.

2. Background

Ension, Inc. (Ension) is a U.S. company specializing in design, development and evaluation of innovative medical products, biocompatible surfaces and biologic scaffolds. Ension has developed and continues to develop proprietary technologies (collectively the Ension Technologies) for "portable Cardiopulmonary Assist Systems" also known as pCAS technologies, and Extracorporeal Membrane Oxygenation also known as ECMO technologies. The Ension designed pCAS and ECMO technologies have implemented Engineered Bioactive Surface Treatment developed by Ension, also known as EBS technologies.

It has been noted that lung disease is the third largest cause of death in the United States of America, accounting for approximately 1 out of every 7 adult deaths. It has been estimated that 30 million Americans are living with chronic lung disease.

Available therapies for patients with chronic respiratory failure include, for example, ventilation and ECMO. Mechanical ventilation is effective for short-term support. Often, however, the excessive tidal volumes, airway pressure, and oxygen fraction necessary to achieve sufficient gas exchange with mechanical ventilation can cause further damage to the lungs, creating ventilator-induced lung injury further exacerbating acute respiratory insufficiency in many patients.

ECMO systems have represented a desired therapy solution since they closely simulate physiological gas exchange. However, historical ECMO systems are complex in operation, can result in thrombosis, blood trauma, infection and bleeding due to the need for high levels of anti-coagulation, and limit patient mobility.

There have been efforts to develop more efficient and compact devices for respiratory and cardiopulmonary support systems. For example, attempts have been made to integrate multiple components of cardiopulmonary, ECMO- systems into single structures so as to eliminate or minimize the need for the extension of lengthy, blood-filled tubes.

Various integrated pump-oxygenators have been described in the prior art as evidenced by U.S. Pat. Nos. 5,217,689; 5,266,265; 5,270,005; 5,770,149; 4,975,247; 5,429,486; 6,963,222; and 6,730,267, which are incorporated herein by reference. There are drawbacks associated with these integrated pump-oxygenators including non-uniform blood flow through the fiber membranes and the existence of laminar boundary flow zones between blood cells and fiber membranes. Non-uniform blood flow across the fiber membranes results in hyper- and hypo-perfusion of the blood in flow paths. Hyper-perfusion does not grant any additional benefit once blood is oxygen-saturated, yet subjects the blood unnecessarily to prolonged exposure to artificial materials, thereby increasing risk of hemolysis and thrombosis. Hyper-perfusion occurs when oxygen-saturated blood is exposed to oxygenator fibers. The exposure to oxygenator fibers does not confer any benefit to the blood because it is already saturated with oxygen. Rather, the exposure unnecessarily increases shear stress and contact with synthetic material. Hypo-perfusion occurs when blood incompletely saturated with oxygen before it is discharged from the oxygenator. In order to combat hypo-perfusion, longer flow paths and fiber membranes having larger surface areas (e.g., 2-4 $m^2$) have historically previously been used, resulting in extended contact of the blood with the fiber membrane surfaces, which, in turn, leads to blood activation thrombosis formation.

In addition, the pumps used in commercial ECMO systems, or proposed to be used in the above patents, all can suffer device-induced blood trauma (hemolysis, and blood element activation) due to the technologies utilized (mechanical bearings, non-optimized flow paths and large prime volume). Efforts to decrease the effect of the boundary layer include increasing shear rate and/or turbulence of the blood flow path by the introduction of secondary flows, for example, by directing blood to flow at a substantial angle, such as perpendicular, to the fiber membranes. U.S. Pat. No. 4,639,353, for example, discloses the use of an arrangement of bundles of hollow fibers perpendicular to the direction of blood flow via a series of flow guide structures.

U.S. Pat. No. 5,263,924 discloses the use of an integrated centrifugal pump and membrane oxygenator comprising hollow fibers, which are displaced circumferentially in a ring around an impeller of the centrifugal pump and through which blood is pumped for oxygenation. Other efforts to decrease the effect of the boundary layer include actively rotating hollow fiber membranes or moving fiber membranes in the path of blood flow. The motion of membrane surfaces relative to the blood cells causes pumping and oxygenation to occur simultaneously and can disrupt the build-up of the boundary layer around the gas-exchange surface. Examples of oxygenators with active gas-exchange membranes include those described in U.S. Pat. Nos. 5,830,370; 6,723,284; and 6,503,450.

U.S. Publication 2015/0352265 proposes an anti and non-thromogenic, heparin—based coating for a surface to be contacted with blood. The quaternary ammonium salt and heparin complex coating of surfaces represent less desirable modification than other surface treatments resulting in covalently bonded heparin surfaces.

Additional patents and publications giving a general overview of conventional blood pump-oxygenators include U.S. Pat. Nos. 6,929,777, 7,927,544, U.S. Publication Nos. 2002-0057989, 2004-0219059, 2007-0249888, 2008-0190870, 2009-0175762, 2010-0101657, and 2010-0288703.

U.S. Patent Publication Number 2008-0199357 describes improvements supported, at least in part, by the National Institutes of Health Small Business Technology Transfer under grant no. NIH R41 HL084807-01 provides an integrated centrifugal blood pump-oxygenator for an extracorporeal life support system addressing these concerns. The blood pump-oxygenator controls is configured for effective blood pumping while minimizing blood trauma, through the use of a bearingless, magnetically levitating and rotating impeller. The blood pump-oxygenator can maintain adult and pediatric pumping and respiratory functions for 14 days or more. There are conceptual advantages to this proposed system but further improvements are still needed. Further it does not appear that any commercial designs were produced under this concept.

A more recent attempt at a compact, efficient and minimally-traumatic pump-oxygenator is disclosed in U.S. Pat. No. 9,211,369 and in earlier associated publication 2013-0343954, which are incorporated herein by reference. This concept teaches an integrated blood pump oxygenator comprising a central housing member defining a central blood flow path extending along a general longitudinal axis of the integrated blood pump oxygenator; a center pump housing member coupled to the central housing member and defining a pump inlet in fluid communication with the central blood flow path; an impeller rotationally received within the area of the pump inlet formed by the central pump housing member, wherein the impeller, inlet and center pump housing member combine to form a centrifugal pump; an impeller housing supporting the impeller and wherein the impeller housing and center pump housing member combine to form a rollover outlet in the form of an annular chamber extending around the center pump housing member; an outer housing coupled to the center pump housing; an annular array of hollow fiber membranes configured for gas transfer within the outer housing; and an annular chamber within the annular array of hollow fiber membranes in fluid communication with the annular chamber extending from the impeller around the center pump housing; wherein the annular chamber provides substantially perpendicular radial outward cross flow across the membranes. This concept expressly utilizes a hydrogel impeller packing material. There are advantages to this system but further improvements are still needed.

All of the above identified patents and patent publications are incorporated herein by reference and yield a comprehensive overview of the state of the art in this field. There remains a need for a compact, efficient, effective adult and pediatric extracorporeal life support system.

SUMMARY OF THE INVENTION

We, Mark Gartner of Ension Inc, Minkyun Noh of the Department of Mechanical Engineering, Massachusetts Institute of Technology, and David Trumper also of the Department of Mechanical Engineering, Massachusetts Institute of Technology have developed an adult and pediatric extracorporeal life support system with heparin treated oxygenator surface and magnetic levitation motor.

One aspect of the invention provides an adult and pediatric extracorporeal life support system comprising: a central housing member defining a blood inlet and a central blood flow path extending along a general longitudinal axis of the system; a center pump housing member coupled to the central housing member and defining a pump inlet in fluid communication with the central blood flow path; an impeller rotationally received within the area of the pump inlet formed by the central pump housing member, wherein the impeller is magnetically supported and magnetically driven; an array of hollow fiber membranes configured for gas transfer within the system for oxygenation of blood flowing across the hollow fiber membranes, wherein the membranes include a covalently-bonded heparin-based bioactive surface, and wherein the blood flow path extends from the impeller to a position to flow perpendicular over the array of hollow fiber membranes; and a blood outlet configured to receive blood flowing past the array of hollow fiber membranes.

The adult and pediatric extracorporeal life support system according to the invention further includes a hysteresis motor supporting and driving the impeller.

The adult and pediatric extracorporeal life support system according to one aspect of the invention may provide wherein the blood outlet is parallel to the blood inlet.

The adult and pediatric extracorporeal life support system according to one aspect of the invention may provide wherein the blood flow path extending from the impeller to a position to flow perpendicular over the array of hollow fiber membranes in configured to deliver blood flow evenly along a length of the hollow fibers.

The adult and pediatric extracorporeal life support system according to one aspect of the invention may provide wherein the membranes are coated with a polysiloxane prior to covalently bonding the heparin, and wherein the polysiloxane surface has been rendered amino functional prior to bonding the heparin.

One aspect of the invention provides an integrated blood pump oxygenator system comprising: a central housing member defining a blood inlet and a central blood flow path extending along a general longitudinal axis of the system; a center pump housing member coupled to the central housing member and defining a pump inlet in fluid communication with the central blood flow path; an impeller rotationally received within the area of the pump inlet formed by the central pump housing member, wherein the impeller is magnetically supported and magnetically driven; an array of hollow fiber membranes configured for gas transfer within the system for oxygenation of blood flowing across the hollow fiber membranes, wherein the membranes include a covalently-bonded heparin-based bioactive surface, and wherein the blood flow path extends from the impeller to a position to flow perpendicular over the array of hollow fiber membranes; and a blood outlet configured to receive blood flowing past the array of hollow fiber membranes.

These and other aspect of the present invention are described in the attached figures in which like reference numerals represent like elements throughout.

DESCRIPTION OF THE PREFERRED EMBODIMENT

Figure 1:
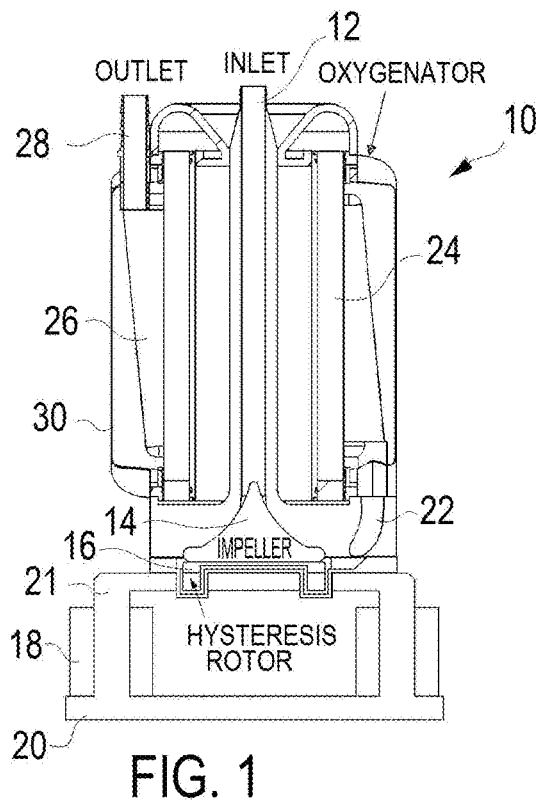
FIG. 1 is a schematic sectional view of an adult and pediatric extracorporeal life support system according to one aspect of the present invention.

The present invention provides an adult and pediatric extracorporeal life support system 10 which includes a central housing member defining a blood inlet 12 and a central blood flow path extending along a general longitudinal axis of the system 10; a center pump housing member coupled to the central housing member and defining a pump inlet in fluid communication with the central blood flow path; an impeller 14 rotationally received within the area of the pump inlet formed by the central pump housing member, wherein the impeller is magnetically supported and magnetically driven by a hysteresis motor; an array of hollow fiber membranes 24 configured for gas transfer within the system 10 for oxygenation of blood flowing across the hollow fiber membranes 24, wherein the membranes 24 include a covalently-bonded heparin-based bioactive surface, and wherein the blood flow path extends from the impeller 14 to a position via conduit 22 to flow perpendicular over the array of hollow fiber membranes 24; and a blood outlet 28 configured to receive blood flowing past the array of hollow fiber membranes 24 into an outlet chamber 26. The blood outlet 28 is parallel to the blood inlet 12 to further provide a compact structure.

As noted the blood flow from the impeller 14 is via appropriate conduits 22 to positions adjacent the membranes 24. The conduits 22 may be tapered to facilitate even flow across the length of the membranes 24 and to assure the flow is perpendicular to the membranes 24. The invention contemplates inside out (radially outward) flow across membranes 24 in which conduit 22 extends to a radially inward chamber within the membranes 24 and the conduit 26 is an annular chamber outside the membranes 24. The invention contemplates outside in (radially inward) flow across membranes 24 in which conduit 22 extends to a radially outward chamber around the membranes 24 and the conduit 26 is an annular chamber inside the membranes 24 with a coupling to the outlet 28. Other arrangements are also possible.

A gas inlet and outlet is provided coupled to the membranes 24 as known in the art for introducing oxygen and removing carbon dioxide from the system 10.

Figure 2:
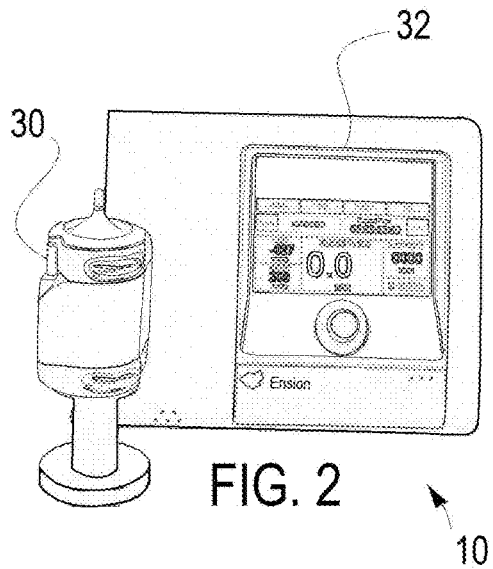
FIG. 2 is a perspective view of the adult and pediatric extracorporeal life support system of FIG. 1.

The present invention provides a highly portable advanced compact pCAS system 10 and ECLS (ACE) system 10 based around an integrated pump-oxygenator, the relative size of which is shown in FIG. 2 with an associated controller 32 and display illustrated.

The hollow fiber membranes 24, as known in the art, are microporous or semipermeable, that is, capable of permitting carbon dioxide and oxygen to permeate through it while at the same time preventing the blood itself from passing therethrough. These hollow fiber membranes 24 may be made out of polymethylpentene, polypropylene or silicone, for example.

The hollow fiber membranes 24 are formed by a large plurality of microporous or semipermeable hollow fibers aligned so that their longitudinal axes are generally parallel to the longitudinal axis of the system 10. It will be understood that carbon dioxide diffuses from the blood flowing outside generally perpendicularly across the hollow fiber membranes 24 through the fiber walls into the stream of oxygenating gas. At the same time, oxygen from the oxygenating gas flowing within the hollow fiber membranes 24 diffuses through the walls of the hollow fibers to oxygenate the blood flowing thereby.

One principal feature of this system is the hollow fiber membranes 24 include an engineered bioactive surface (EBS) in the form of a covalently-bonded heparin-based bioactive surface. The aspects of this process in general are described in greater detail in U.S. Pat. Nos. 8,114,465 and 8,343,567 which are incorporated herein by reference. Here the particular covalently-bonded heparin-based bioactive surface satisfies the unique requirements of ECLS applications. The covalently-bonded heparin-based bioactive surface as described is designed to mitigate activation of cellular elements in the blood, development of thrombi, and minimize overall systemic inflammatory response and validated extensively including ISO 10993 testing.

According to the present invention, a process for preparing the fiber membranes 24 coated with heparin includes coating the membranes 24 with a polysiloxane; rendering the polysiloxane surface amino functional; and contacting the amino-functional polysiloxane surface with heparin under conditions effective to covalently bond the heparin to the hollow fiber membranes 24.

The surface of the resulting coated membranes 24 remains permeable to oxygen and carbon dioxide during exposure to blood by, in part, preventing adhesion of phospholipids.

The process may include a step of cleaning the membranes 24 prior to polysiloxane coating application to remove any surface contaminants or impurities. Such cleaning may be done, for example, by placing the membranes 24 in a plasma chamber, infusing air, oxygen, and/or nitrogen into the plasma chamber, and then exposing the membranes 24 to plasma energy.

The polysiloxane coating step may be accomplished in any of several manners. It is possible to contact the membranes 24 with a polysiloxane in a liquid carrier. Contact may be by brushing, dipping (immersion), flow coating, spraying and the like. Immersion may include stirring or other agitation of the coating composition, by use of a stirring device or by movement of the membranes 24 to be coated through the composition. More often, however, the membranes 24 is exposed to a reactive gas containing siloxane functional groups and plasma energy to yield a plasma-deposited polysiloxane surface on the membranes 24. The plasma-deposited surface comprises a polymeric layer deposited onto the substrate. Siloxane molecules are fragmented in the plasma phase and recombine to yield a high molecular weight polymeric compound that deposits as a film on the surface of the membranes 24.

Rendering the polysiloxane surface of the treated membranes 24 amino functional generally comprises contacting the polysiloxane surface with an amino- and/or imino-functional compound for a time sufficient to effect adsorption of the amino- and/or imino-functional compound onto the polysiloxane surface. In such embodiments, the amino- and/or imino-functional compound may comprise polyethyleneimine, an amino-functional silane and/or diaminopropane. Examples of suitable amino functional silanes include amino-functional silanes sold as the Dow Corning Z-silane series. Depending on the identity of the compound, it may be present in a liquid carrier, particularly when the compound is an amino-functional silane. Again, contact may be by brushing, dipping (immersion), flow coating, spraying and the like, but is typically by immersion. After adsorption of the compound onto the surface, any imino-functional groups may be reduced to amino-functional groups by addition of a suitable reducing agent to the liquid carrier.

Alternatively, rendering the polysiloxane surface of the treated membranes 24 amino functional may comprise exposing the plasma-deposited polysiloxane surface to ammonia or an organic amino-functional gas and to plasma energy to yield an amino-functional plasma-deposited surface. Suitable organic amino-functional gases include amino-functional polysiloxane, diaminopropane, and allyl amine.

Prior to attachment of the heparin to the amino-functional polysiloxane surface it may be desirable to expose the amino-functional polysiloxane surface to a reactive gas containing acrylic acid and to plasma energy to yield a plasma-deposited polyacrylic acid coating on the surface.

The amino-functional polysiloxane surface of the membranes 24 is contacted with heparin under conditions effective to covalently bond the heparin to the membranes 24. Attachment of the heparin to the amino-functional polysiloxane surface can be accomplished by any of a number of methods known to those skilled in the art. One particularly preferred method is an oxidation method involving the use of periodate. The heparin, is contacted with a periodate in a buffered aqueous solution and allowed to react. This controlled oxidation provides a limited number of reactive aldehyde groups per molecule. The periodate is a water-soluble periodate, preferably, an alkali metal periodate, such as sodium periodate. The amount of periodate used is sufficient to react with no more than two of the sugar units in the heparin molecule (i.e., the basic disaccharide residues constituting the structure of the glycosaminoglycan). If the periodate used is sodium periodate and the heparin used is a commercially available injectable form of heparin (e.g., its sodium salt with activity of 160 units/milligram), the weight ratio of heparin to periodate should be about 30:1 or less in order to react with no more than two of the sugar units in the heparin molecule. It will be appreciated by those skilled in the art that the amount of periodate required for other periodate compounds and other forms of heparin can be determined by conventional calculation and empirical tests.

The reaction between heparin and periodate takes place in an aqueous buffer solution. Generally, buffers having a pH in a neutral to slightly acidic range of about 4.5 to about 8 can be used. A lower pH (e.g., an acetate buffer at pH 4.5) is preferred if a rapid reaction is desired while a more neutral pH (e.g., a phosphate buffer at pH 6.88) is preferred for a slower reaction with a longer storage life. With the acetate buffer at a pH of 4.5, the reaction should proceed for about 3 hours, while with a phosphate buffer at a pH or 6.88, the reaction should proceed for about 16 hours. If desired, the reacted mixture may then be stored prior to use at about 5 degrees C.

The reacted mixture is diluted and the pH adjusted in order to bring the pH of the mixture to a pH that is favorable for the coupling reaction between the heparin and the amino-functional polysiloxane. A mild reducing agent, such as sodium cyanoborohydride, is added to the diluted mixture to effect the reduction of the bonds formed between the reactive aldehyde groups on the oxidized biomolecule and the amine functional groups on the polysiloxane coated on the substrate surface. The surface of the treated membranes 24 is then contacted with (e.g., immersed in or flushed with) the diluted mixture at a sufficient temperature and for a sufficient time to complete the reaction (i.e., attach the heparin).

Figure 3:
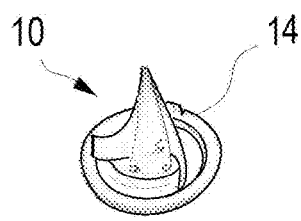
FIG. 3 is a perspective view of a magnetically levitated and driven impeller used in the adult and pediatric extracorporeal life support system of FIG. 1.

Another aspect of the invention is the magnetic levitation for the impeller 14 (shown separately in FIG. 3) of the Extracorporeal Life Support (ECLS). Magnetic levitation enables contact-free impeller 14 rotation against the pump housing, thereby eliminating critical areas of wear and heat generation that can contribute to hemolysis and thrombosis in ECLS.

The current ECLS market is mainly served by permanent-magnet-based blood pumps such as CentriMag and PediMag from St. Jude Medical's (formerly Thoratec). While these products have been used successfully in a range of post-cardiotomy support applications, broader usage is complicated by several factors including: Lack of ancillary componentry designed specifically for the ECLS applications, e.g., blood oxygenators and heat exchanger; complex control algorithms; and high disposable costs.

The present invention utilizes a magnetic levitation/drive system for ECLS blood pump applications based on a hysteresis motor concept. The advantages of hysteresis levitation/drive over permanent magnet-based motor include: Significant reduction in material and manufacturing costs due to elimination of rare-earth magnets yielding a potentially lower disposable cost; Elimination of permanent magnet-related magnetic field interference concerns; Vibration reduction during the rotation due to the inherent characteristic of smooth torque generation and axisymmetric rotor geometry; and Simplified control algorithms and reduced power requirements for suspension.

Figure 4:
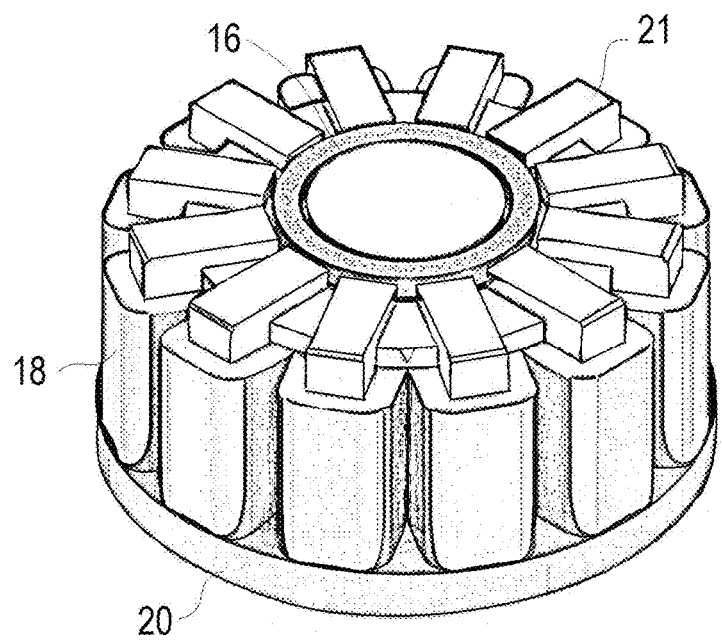
FIG. 4 is a perspective view of a hysteresis motor used in the adult and pediatric extracorporeal life support system of FIG. 1.

The system 10 uses bearingless motor based upon a homopolar flux-biased magnetic bearing for force generation and a hysteresis motor for torque generation. The bearingless slice motor shown in FIG. 4 levitates and rotates the ring-shaped rotor 16 made of a semi-hard magnetic material. Stator coils 18 on a base plate 20 with teeth 21 form the motor. Torque is generated by a hysteretic coupling between the rotor 16 and a rotating multi-pole stator field. Similar bearingless slice motors have been developed over 20 years ago, see Barletta N., Schöb R., Design of a Bearingless Blood Pump, Proc. of the 3rd Int, Symp. On Magnetic Suspension Technology, Tallahassee, 1995. The specific operation and control for the slice motor shown is described in U.S. Patent Publication 2017-0040868 which is incorporated herein by reference.

The design illustrates an effective adult and pediatric extracorporeal life support system 10 with heparin treated oxygenator surface on membranes 24 and magnetic levitation motor for impeller 14. Specifically the system provides a highly portable advanced compact ECLS (ACE) system 10 based around a unique efficient and effective integrated pump-oxygenator. The system 10 includes an engineered bioactive surface formed as a covalently-bonded heparin-based bioactive surface and designed to mitigate activation of cellular elements in the blood, development of thrombi, and minimize overall systemic inflammatory response. The system 10 includes a magnetic levitation/drive system utilizing a hysteresis motor.

The pump-oxygenator system 10 that may be considered modular, accommodates both pediatric and adult applications that is suitable for both short-term (e.g., intraoperative cardiopulmonary bypass) and chronic applications such as ECMO, extracorporeal lung assist, and extracorporeal $CO_2$ removal ($ECCO_2R$)

It will be apparent to those of ordinary skill in the art that various modifications to the present invention may be made without departing from the spirit and scope of the present invention.

What is claimed is:

1. An extracorporeal life support system comprising:
   a central housing member defining a blood inlet and a central blood flow path extending along a general longitudinal axis of the system;
   a center pump housing member coupled to the central housing member and defining a pump inlet in fluid communication with the central blood flow path;
   an impeller rotationally received within the area of the pump inlet formed by the central pump housing member, wherein the impeller is magnetically supported and magnetically driven;
   an array of hollow fiber membranes configured for gas transfer within the system for oxygenation of blood flowing radially outwardly across the array of the hollow fiber membranes, wherein each of the hollow fiber membranes of the array of the hollow fiber membranes includes a covalently-bonded heparin-based bioactive surface, and wherein the central blood flow path extends from the impeller to a position to flow perpendicular radially outwardly over the array of the hollow fiber membranes; and
  a blood outlet configured to receive the blood flowing radially outwardly past the array of the hollow fiber membranes.

2. The extracorporeal life support system according to claim 1 further including a hysteresis motor supporting and driving the impeller.

3. The extracorporeal life support system according to claim 2 wherein the blood outlet is parallel to the blood inlet.

4. The extracorporeal life support system according to claim 3 wherein the central blood flow path extending from the impeller to a position to flow perpendicular over the array of the hollow fiber membranes is configured to deliver blood flow evenly along a length of the hollow fiber membranes of the array of the hollow fiber membranes.

5. The extracorporeal life support system according to claim 4 wherein each of the hollow fiber membranes of the array of the hollow fiber membranes is treated with a polysiloxane forming a polysiloxane surface prior to covalently bonding the heparin-based bioactive surface.

6. The extracorporeal life support system according to claim 5 wherein the polysiloxane surface has been rendered amino functional prior to bonding the heparin-based bioactive surface.

7. The extracorporeal life support system according to claim 1 wherein the blood outlet is parallel to the blood inlet.

8. The extracorporeal life support system according to claim 7 wherein the central blood flow path extending from the impeller to a position to flow perpendicular over the array of the hollow fiber membranes is configured to deliver blood flow evenly along a length of the hollow fiber membranes of the array of the hollow fiber membranes.

9. The extracorporeal life support system according to claim 1 wherein each of the hollow fiber membranes of the array of the hollow fiber membranes is treated with a polysiloxane forming a polysiloxane surface prior to covalently bonding the heparin-based bioactive surface.

10. The extracorporeal life support system according to claim 9 wherein the polysiloxane surface has been rendered amino functional prior to bonding the heparin-based bioactive surface.

11. An integrated blood pump oxygenator system comprising:
  a central housing member defining a blood inlet and a central blood flow path extending along a general longitudinal axis of the system;
  a center pump housing member coupled to the central housing member and defining a pump inlet in fluid communication with the central blood flow path;
  an impeller rotationally received within the area of the pump inlet formed by the central pump housing member, wherein the impeller is magnetically supported and magnetically driven;
  an array of hollow fiber membranes configured for gas transfer within the system for oxygenation of blood flowing radially outwardly across the array of the hollow fiber membranes, wherein each of the hollow fiber membranes of the array of the hollow fiber membranes includes a covalently-bonded heparin-based bioactive surface, and wherein the central blood flow path extends from the impeller to a position to flow radially outwardly perpendicular over the array of the hollow fiber membranes; and
  a blood outlet configured to receive the blood flowing radially outwardly past the array of the hollow fiber membranes.

12. The integrated blood pump oxygenator system according to claim 11 further including a hysteresis motor supporting and driving the impeller.

13. The integrated blood pump oxygenator system according to claim 11 wherein the blood outlet is parallel to the blood inlet.

14. The integrated blood pump oxygenator system according to claim 11 wherein the central blood flow path extending from the impeller to a position to flow perpendicular over the array of the hollow fiber membranes is configured to deliver blood flow evenly along a length of the hollow fiber membranes of the array of the hollow fiber membranes.

15. The integrated blood pump oxygenator system according to claim 11 wherein each of the hollow fiber membranes of the array of the hollow fiber membranes is treated with a polysiloxane forming a polysiloxane surface prior to covalently bonding the heparin-based bioactive surface.

16. The integrated blood pump oxygenator system according to claim 15 wherein the polysiloxane surface has been rendered amino functional prior to bonding the heparin-based bioactive surface.

17. An integrated blood pump oxygenator system comprising:
  a central housing member defining a blood inlet and a central blood flow path extending along a general longitudinal axis of the system;
  a center pump housing member coupled to the central housing member and defining a pump inlet in fluid communication with the central blood flow path;
  an impeller rotationally received within the area of the pump inlet formed by the central pump housing member, wherein the impeller is magnetically supported and magnetically driven;
  a hysteresis motor supporting and driving the impeller;
  an array of hollow fiber membranes configured for gas transfer within the system for oxygenation of blood flowing radially outwardly across the array of the hollow fiber membranes, wherein each of the hollow fiber membranes of the array of the hollow fiber membranes includes a covalently-bonded heparin-based bioactive surface, and wherein the central blood flow path extends from the impeller to a position to flow radially outwardly perpendicular over the array of the hollow fiber membranes; and
  a blood outlet configured to receive the blood flowing radially outwardly past the array of the hollow fiber membranes, wherein the blood outlet is parallel to the blood inlet.

18. The integrated blood pump oxygenator system according to claim 17 wherein each of the hollow fiber membranes of the array of the hollow fiber membranes is treated with a polysiloxane forming a polysiloxane surface prior to covalently bonding the heparin-based bioactive surface.

19. The integrated blood pump oxygenator system according to claim 18 wherein the polysiloxane surface has been rendered amino functional prior to bonding the heparin-based bioactive surface.

20. The integrated blood pump oxygenator system according to claim 18 wherein the central blood flow path extending from the impeller to a position to flow perpendicular over the array of the hollow fiber membranes is configured to deliver blood flow evenly along a length of the hollow fiber membranes of the array of the hollow fiber membranes.

\* \* \* \* \*